(12) United States Patent
Halm (10) Patent No.: US 11,351,309 B2
(45) Date of Patent: Jun. 7, 2022

(54) MEDICAMENT INJECTION DEVICE

(71) Applicant: Sanofi-Aventis Deutschland GMBH, Frankfurt am Main (DE)

(72) Inventor: Markus Halm, Frankfur am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 262 days.

(21) Appl. No.: 16/344,430

(22) PCT Filed: Oct. 23, 2017

(86) PCT No.: PCT/EP2017/077018
§ 371 (c)(1),
(2) Date: Apr. 24, 2019

(87) PCT Pub. No.: WO2018/077809
PCT Pub. Date: May 3, 2018

(65) Prior Publication Data
US 2020/0054839 A1    Feb. 20, 2020

(30) Foreign Application Priority Data

Oct. 25, 2016 (EP) .................... 16195413

(51) Int. Cl.
*A61M 5/32* (2006.01)
*A61M 5/20* (2006.01)
*A61M 5/24* (2006.01)

(52) U.S. Cl.
CPC ........ *A61M 5/3204* (2013.01); *A61M 5/2033* (2013.01); *A61M 5/2466* (2013.01);
(Continued)

(58) Field of Classification Search
CPC .......... A61M 5/3204; A61M 2005/247; A61M 5/2466; A61M 2005/2411; A61M 5/2033;
(Continued)

(56) References Cited

U.S. PATENT DOCUMENTS 5,478,316 A * 12/1995 Bitdinger ............ A61M 5/2033
604/135
5,658,259 A * 8/1997 Pearson .............. A61M 5/2033
604/136
(Continued)

FOREIGN PATENT DOCUMENTS

CN    101193674    6/2008
CN    101687079    3/2010
(Continued)

OTHER PUBLICATIONS

International Preliminary Report on Patentability in Application No. PCT/EP2017/077018, dated Apr. 30, 2019, 9 pages.
(Continued)

*Primary Examiner* — Nathan R Price
*Assistant Examiner* — Mark A Igel
(74) *Attorney, Agent, or Firm* — Fish & Richardson P.C.

(57) ABSTRACT

A medicament injection device is disclosed comprising a housing containing a medicament cartridge holder; a rotatable cap assembly; a needle holder holding a needle, the needle holder being releasably supported by the cap assembly, a pre-stressed spring coupled to the medicament cartridge holder; wherein the cap assembly is arranged so that rotation thereof releases the pre-stressed spring, causing the medicament cartridge holder to move axially in a distal direction towards the needle. A method of operating the device is also disclosed.

19 Claims, 3 Drawing Sheets

(52) U.S. Cl.
CPC ............ *A61M 2005/206* (2013.01); *A61M 2005/2026* (2013.01); *A61M 2005/247* (2013.01)

(58) Field of Classification Search
CPC ........ A61M 2005/2026; A61M 5/2455; A61M 5/285
See application file for complete search history.

(56) References Cited

U.S. PATENT DOCUMENTS

| | | | | |
|---|---|---|---|---|
| 5,928,205 | A * | 7/1999 | Marshall | A61M 5/348 604/263 |
| 10,335,535 | B2 * | 7/2019 | Bengtsson | A61M 5/3213 |
| 2003/0144633 | A1 * | 7/2003 | Kirchhofer | A61M 5/326 604/201 |
| 2014/0025014 | A1 * | 1/2014 | Radmer | A61M 5/002 604/198 |
| 2015/0094684 | A1 | 4/2015 | Kriesel et al. | |
| 2015/0335829 | A1 * | 11/2015 | Giambattista | A61M 5/2033 604/192 |
| 2015/0367072 | A1 * | 12/2015 | Constantineau | A61M 5/3202 604/518 |
| 2017/0007775 | A1 * | 1/2017 | Bengtsson | A61M 5/24 |
| 2017/0014575 | A1 * | 1/2017 | Hansen | A61M 5/20 |
| 2018/0369498 | A1 * | 12/2018 | Schader | A61M 5/3243 |
| 2020/0129697 | A1 * | 4/2020 | Helmer | A61M 5/2466 |

FOREIGN PATENT DOCUMENTS

| | | | | |
|---|---|---|---|---|
| CN | 102458515 | | 5/2012 | |
| CN | 103118723 | | 5/2013 | |
| CN | 103167887 | | 6/2013 | |
| CN | 103269730 | | 8/2013 | |
| CN | 104428020 | | 3/2015 | |
| CN | 104968381 | | 10/2015 | |
| CN | 105636625 | | 6/2016 | |
| CN | 105658256 | | 6/2016 | |
| EP | 1044698 | A1 * | 10/2000 | ......... A61M 5/5086 |
| EP | 2944340 | | 11/2015 | |
| JP | 2014-503298 | | 2/2014 | |
| WO | WO 96/30065 | | 10/1996 | |
| WO | WO 97/14455 | | 4/1997 | |
| WO | WO 2006/082350 | | 8/2006 | |
| WO | WO 2009/007305 | | 1/2009 | |
| WO | WO 2010/149975 | | 12/2010 | |
| WO | WO 2012/022810 | | 2/2012 | |
| WO | WO 2012/089821 | | 7/2012 | |
| WO | WO-2012135524 | A1 * | 10/2012 | ............. A61P 29/00 |
| WO | WO 2014/001318 | | 1/2014 | |
| WO | WO 2014/095424 | | 6/2014 | |
| WO | WO-2014095424 | A1 * | 6/2014 | ......... A61M 5/3204 |
| WO | WO 2015/117854 | | 8/2015 | |
| WO | WO 2015/150578 | | 10/2015 | |
| WO | WO 2015/173167 | | 11/2015 | |
| WO | WO 2016/028814 | | 2/2016 | |

OTHER PUBLICATIONS

International Search Report and Written Opinion in Application No. PCT/EP2017/077018, dated Dec. 22, 2017, 14 pages.

* cited by examiner

MEDICAMENT INJECTION DEVICE

CROSS REFERENCE TO RELATED APPLICATIONS

The present application is the national stage entry of International Patent Application No. PCT/EP2017/077018, filed on Oct. 23, 2017, and claims priority to Application No. EP 16195413.6, filed on Oct. 25, 2016, the disclosures of which are incorporated herein by reference.

TECHNICAL FIELD

The present disclosure relates to medicament injection devices.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

According to a first aspect, this specification provides a medicament injection device comprising:
- a housing containing a medicament cartridge holder;
- a sleeve;
- a rotatable cap assembly comprising a stopping element;
- a needle holder holding a needle, the needle holder being releasably supported by the cap assembly,
- a pre-stressed spring coupled to the housing and to the sleeve;
- wherein the cap assembly is arranged so that rotation thereof causes the stopping element to disengage from the sleeve, thereby releasing the pre-stressed spring and causing the sleeve and the medicament cartridge holder to move axially in a distal direction towards the needle.

The cap assembly may comprise at least one radial rib arranged to prevent axial movement of the medicament cartridge holder prior to rotation of the cap assembly.

The needle holder may comprise a penetrable sealing member arranged to seal a proximal end of the needle.

The medicament cartridge holder may comprise at least one cutting element at a distal end thereof for penetrating the sealing member.

The cap assembly and the housing may be provided with a cap assembly locking mechanism to prevent removal of the cap assembly prior to rotational alignment of the cap assembly with the housing.

The cap assembly may contain an outer needle guard attached at a distal end thereof to the cap and releasably coupled to the needle holder.

The device may further comprise an inner needle guard located inside the outer needle guard and coaxial therewith, wherein the inner needle guard receives a distal end of the needle.

The inner needle guard may be arranged to decouple from the cap assembly when the cap assembly is removed.

The needle holder may have a cup-shaped part arranged to fit over a part of a medicament cartridge.

The device may be an autoinjector device.

The medicament cartridge may contain a medicament.

According to a second aspect, this specification provides a method of operating a medicament injection device having a rotatable cap assembly, the method comprising:
rotating the cap assembly to cause a stopping element to disengage from a sleeve to releasing a pre-stressed spring coupled to a housing and the sleeve, thereby causing the sleeve and a medicament cartridge holder to move axially in a distal direction towards the proximal end of a needle.

The medicament cartridge holder may contain a medicament cartridge and axial movement of the medicament cartridge holder in a distal direction may cause the proximal end of the needle to penetrate a penetrable barrier at the distal end of the medicament cartridge.

Axial movement of the medicament cartridge holder in a distal direction may cause a needle holder to dock with the medicament cartridge.

BRIEF DESCRIPTION OF THE FIGURES

Exemplary embodiments of the present disclosure are described with reference to the accompanying drawings, in which.

DETAILED DESCRIPTION

Embodiments of the disclosure provide a mechanism for inserting the needle of an injection device such as a cartridge auto-injector (CAI) or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments of the disclosure the user does not need to touch the needle during the steps of inserting the needle into the medicament cartridge and subsequently actuating the injection of the medicament.

Embodiments of the disclosure make the needle insertion mechanism dependent on the removal of the device cap. A pre-stressed spring is coupled to medicament cartridge holder and to the housing. After assembly of the device and during storage, the fixation of the spring keeps the needle separate from the medicament cartridge. As the cap is removed, the spring is released causing the medicament cartridge holder to move towards a distal end of the device so that the needle pierces the septum of the medicament cartridge.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
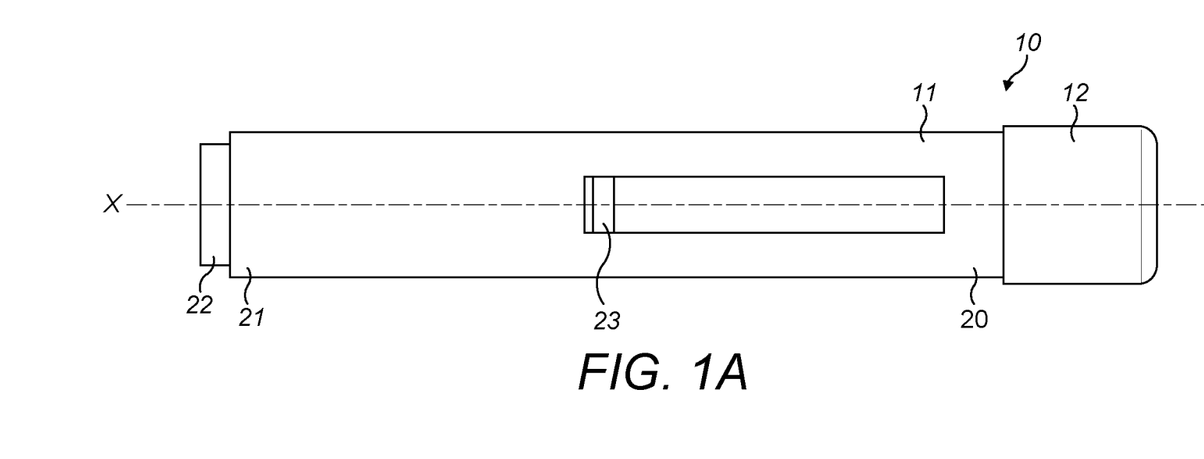
FIGS. 1A and 1B are side-on views of an auto-injector device according to embodiments of the disclosure.
Figure 1B:
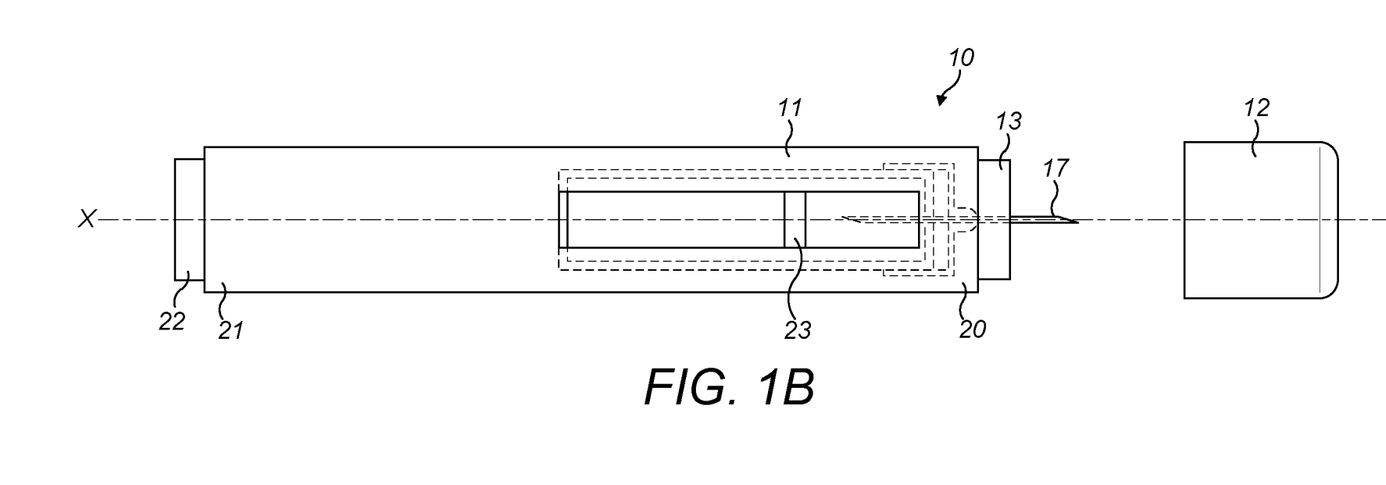

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21.

The term "distal" refers to a location that is relatively closer to a site of injection, and the term "proximal" refers to a location that is relatively further away from the injection site.

Device 10 can also include a sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
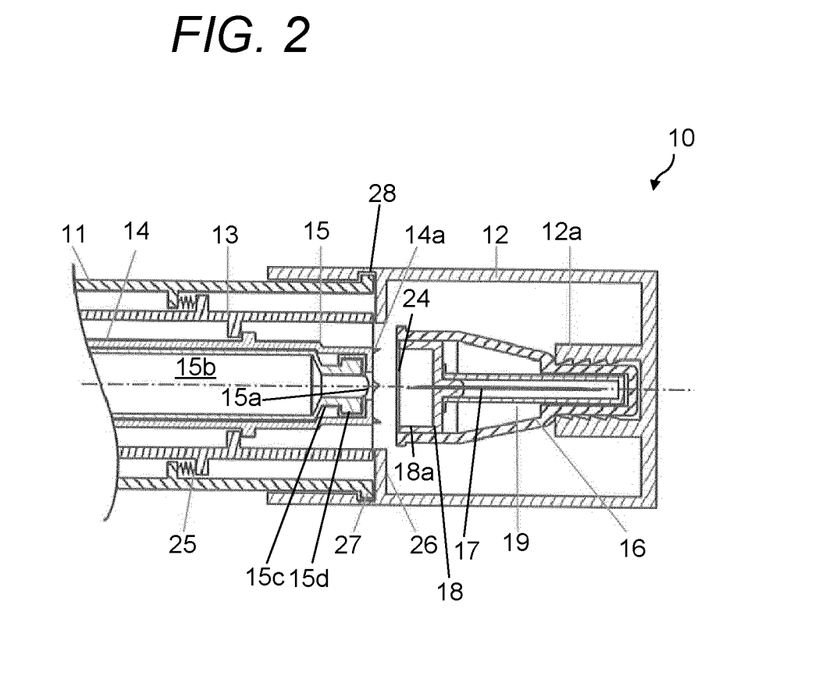
FIG. 2 is a side-on cross sectional schematic view of a distal end of a device prior to cap rotation.

FIG. 2 is a cross-sectional view of the distal end of the device 10. The housing 11 contains a coaxial hollow cylindrical medicament cartridge holder 14 which is axially movable with respect to the housing 11 and the cap 12. The medicament cartridge holder 14 is arranged to hold a medicament cartridge 15 having a penetrable septum 15a at a distal end thereof. The cartridge 15 has a cartridge body 15b a neck 15c and a head 15d. The head 15d is wider than the neck 15c, thereby forming a flanged end. The neck 15c and head 15d contain a passage allowing medicament to pass therethrough as well as to receive a proximal end of the needle 17 once inserted therein. The septum 15a is arranged to close off the passage and to seal the contents of the medicament cartridge 15. The cartridge body 15b, neck 15c and head 15d may be generally cylindrical in shape. However, alternative shapes may be employed.

The cap 12 fits over the sleeve 13 and the housing 11. The cap 12 has an end wall and a curved side wall. The cap 12 comprises a tubular fixing member 12a extending from the end wall of the cap 12. The tubular member is of a suitable diameter to receive an outer needle guard 16 in which the distal end of the needle 17 is stored. A frictional fit is formed between the tubular fixing member 12a and the needle guard 16 containing the distal end of the needle 17 during assembly of the device 10. The frictional fit is sufficiently strong so that, as the cap 12 is removed, the needle guard 16 is also removed. The fit between the tubular member 12a and the needle guard 16 may be provided using clips. Alternatively, the needle guard 16 may be formed out of thermoplastic elastomer (TPE) which is moulded on to the cap 12 using an adhesive bond or glued thereto. Indeed, in some embodiments no tubular member 12a is provided and the needle guard 16 is attached to the main body of the cap 12.

The distal end of the needle 17 is protected by an inner needle guard 19 which is coaxial with respect to the outer needle guard 16. The inner needle guard 19 is releasably held by the outer needle guard 16.

The needle 17 is held towards the proximal end of the needle 17 by a needle holder 18. The needle holder 18 has a generally cup-shaped portion 18a and a passage through which the needle 17 passes. The cup-shaped portion 18a is shaped to engage with the distal end of the medicament cartridge holder 14 subsequent to the insertion of the proximal end of the needle 17 into the cartridge 15.

In some embodiments, the neck 15c and head 15d of the medicament cartridge 15 protrudes from the distal end of the medicament cartridge holder 14. The cup-shaped portion 18a of the needle holder 18 may comprise a lip which serves to clip onto the head 15d of the medicament cartridge 15 to prevent detachment of the needle holder 18 from the cartridge 15 subsequent to the attachment of the needle holder 18 to the cartridge 15.

The curved wall of the cup-shaped portion 18a surrounds the proximal end of the needle 17. A penetrable sealing member 24 such as a foil sheet may be attached to the proximal end of the curved wall of the cup-shaped portion 18a, thereby sealing the proximal end of the needle 17. The medicament cartridge holder 14 comprises one or more cutting elements 14a to penetrate the sealing member 24 upon axial movement of the medicament cartridge holder 14 in the distal direction.

One or more springs 25 are coupled at a first end thereof to the housing 11 and, at a second end thereof, to the sleeve 13. As shown in FIG. 2, the spring 25 is compressed. The spring 25 is held in the compressed state by the cap 12 which comprises at least one stopping element 26 such as a rib extending radially inwardly from the curved wall of the cap 12. As such, as shown in FIG. 2, the distal end of the medicament cartridge 15 is separated along the main axis X of the device 10 from the proximal end of the needle 17.

The device 10 comprises a bayonet locking arrangement between the housing 11 and the cap 12. As shown in FIG. 2, the housing 11 has a pin 27 and the interior of the cap 12 is provided with a slotted link 28. However, in alternative embodiments, the cap 12 may be provided with a pin and the housing 11 provided with a slotted link. The slotted link 28 is a groove having a circumferential length extending along part of the inside of the curved wall of the cap 12 and an axial length extending from the circumferential length to the proximal end of the cap 12. The engagement between the pin 27 and the slotted link 28 prevents removal of the cap 12 prior to rotation of the cap 12 with respect to the housing 11.

Figure 3:
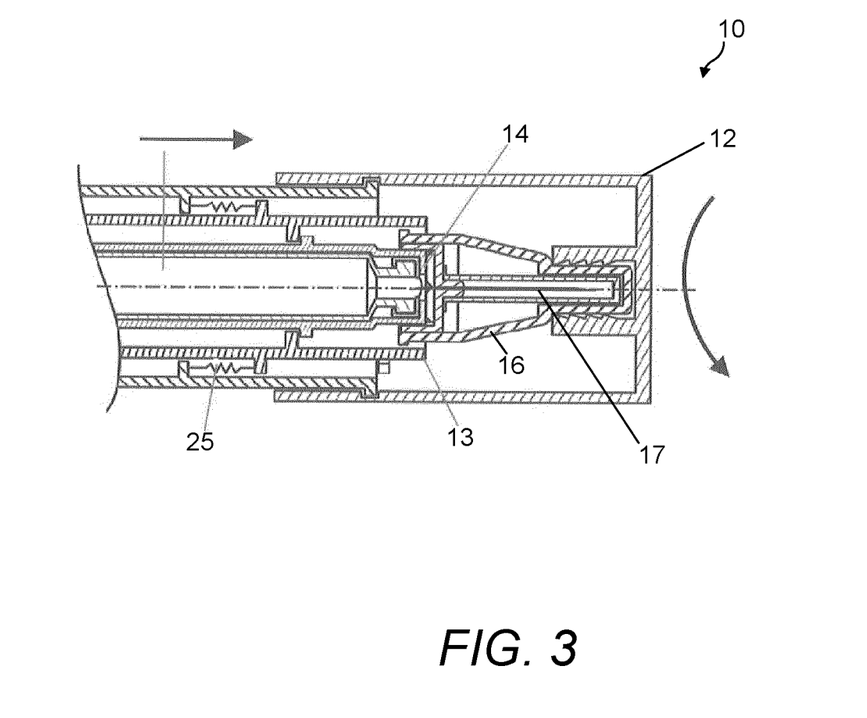
FIG. 3 is a side-on cross sectional schematic view of a distal end of a device as the cap is rotated.

FIG. 3 shows the cap 12 being rotated. As the cap 12 is rotated, the stopping element 26 disengages from the distal end of the sleeve 13. This releases the compressed spring 25 so that the sleeve 13 and the medicament cartridge holder 14 are displaced axially towards the distal end of the device 10. The cutting elements 14a penetrate the sealing member 24. The 10 proximal end of the needle 17 penetrates the septum 15a of the medicament cartridge 15. The cup-shaped portion 18a of the needle holder 18 fits over the distal end of the medicament cartridge holder 14 (or the head 15d of the medicament cartridge 15).

Figure 4:
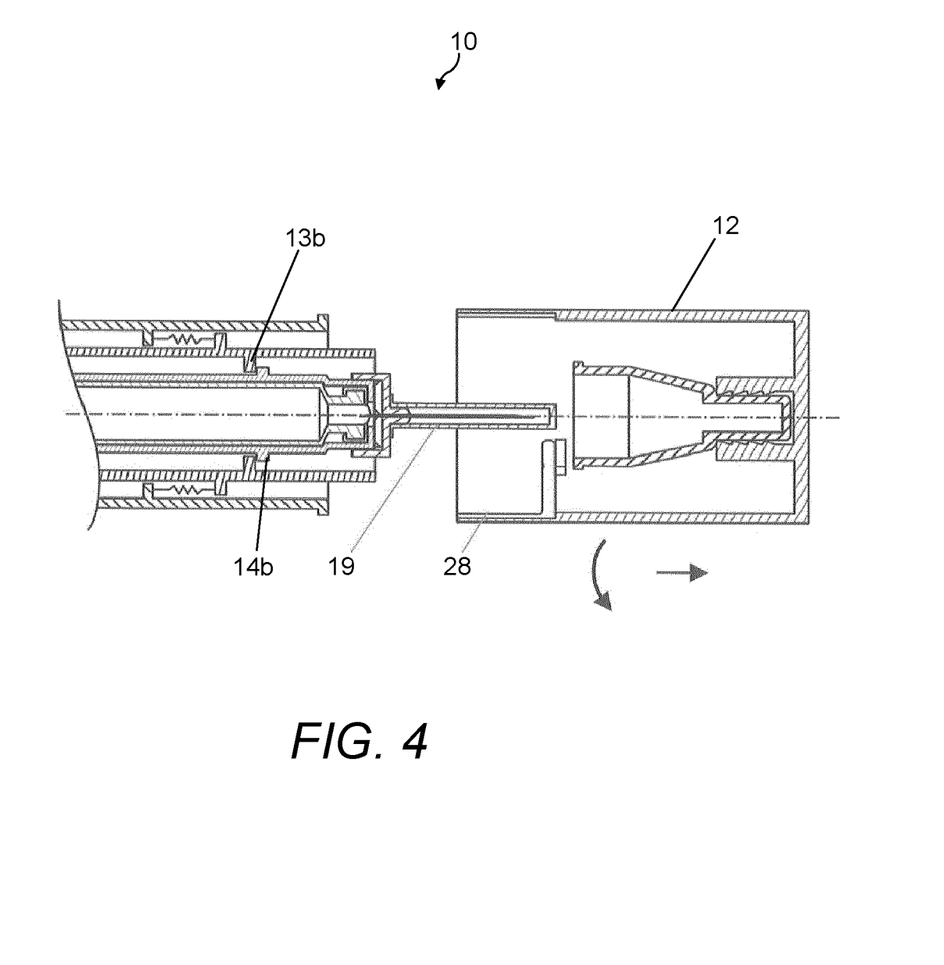
FIG. 4 is a side-on cross sectional schematic view of a distal end of a device as the cap is being removed.

Further rotation of the cap 12 with respect to the housing 11 leads to alignment of the pin 27 with the axial length of the slotted link 28. The cap 12 may then be removed by pulling axially in a distal direction, as shown in FIG. 4. The outer needle guard 16 is removed with the rest of the cap 12. The inner needle guard 19 remains attached to the needle holder 18 and covers the distal end of the needle 17. The inner needle guard 19 may then be removed by the user to expose the distal end of the needle. The injection may then be commenced.

For further needle safety, the sleeve 13 may be activated together with triggering of the power pack. In the embodiments shown in FIGS. 2-4, the sleeve 13 can be activated by a small rotation of itself with respect to the cartridge holder 14, so engagement between cooperating ribs 13b, 14b provided on the sleeve 13 and cartridge holder 14 is released. The cartridge holder 14 may remain in the same position with respect to the housing 11 due to a stop rib (not shown) between the housing 11 and the cartridge holder 14.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, $15^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin;

B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(w-carboxyheptadecanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab). Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A medicament injection device comprising:
   a housing containing a medicament cartridge holder;
   a sleeve;
   a rotatable cap assembly comprising a stopping element;
   a needle holder holding a needle, the needle holder being in releasable direct contact with the rotatable cap assembly; and
   a pre-stressed spring coupled to the housing and to the sleeve,
   wherein the rotatable cap assembly is arranged so that rotation thereof causes the stopping element to disengage from the sleeve, thereby releasing the pre-stressed spring and causing the sleeve and the medicament cartridge holder to move axially in a distal direction towards the needle, and
   wherein the rotatable cap assembly is releasably attached to a distal end of the housing and the needle holder is arranged to fit over a distal part of a medicament cartridge.

2. The medicament injection device of claim 1, wherein the rotatable cap assembly comprises at least one radial rib arranged to prevent axial movement of the medicament cartridge holder prior to rotation of the rotatable cap assembly.

3. The medicament injection device of claim 1, wherein the needle holder comprises a penetrable sealing member arranged to seal a proximal end of the needle.

4. The medicament injection device of claim 3, wherein the medicament cartridge holder comprises at least one cutting element at a distal end thereof for penetrating the penetrable sealing member.

5. The medicament injection device of claim 1, wherein the rotatable cap assembly and the housing are provided with a cap assembly locking mechanism for preventing removal of the rotatable cap assembly prior to rotational alignment of the rotatable cap assembly with the housing.

6. The medicament injection device of claim 1, wherein the rotatable cap assembly contains an outer needle guard attached at a distal end thereof to a cap and releasably coupled to the needle holder.

7. The medicament injection device of claim 6, further comprising an inner needle guard located inside the outer needle guard and coaxial therewith, wherein the inner needle guard receives a distal end of the needle.

8. The medicament injection device of claim 7, wherein the inner needle guard is arranged to decouple from the rotatable cap assembly when the rotatable cap assembly is removed.

9. The medicament injection device of claim 1, wherein the needle holder has a cup-shaped part arranged to fit over a part of the medicament cartridge.

10. The medicament injection device of claim 1, wherein the medicament injection device is an autoinjector device.

11. The medicament injection device of claim 9, wherein the medicament cartridge contains a medicament.

12. The medicament injection device of claim 1, wherein the rotatable cap assembly comprises an outer needle guard releasably coupled to the needle holder.

13. The medicament injection device of claim 12, wherein the outer needle guard is in frictional contact with the rotatable cap assembly.

14. The medicament injection device of claim 1, wherein, prior to the rotation of the rotatable cap assembly, the needle is contained within the rotatable cap assembly.

15. The medicament injection device of claim 1, wherein the rotatable cap assembly is releasably attached to the distal end of the housing by a bayonet locking arrangement.

16. A method of operating a medicament injection device having a rotatable cap assembly, the method comprising:
rotating the rotatable cap assembly to cause a stopping element to disengage from a sleeve for releasing a pre-stressed spring coupled to a housing and the sleeve, thereby causing the sleeve and a medicament cartridge holder to move axially in a distal direction towards a proximal end of a needle,
wherein the rotatable cap assembly is in releasable direct contact with a needle holder and wherein the rotatable cap assembly is releasably attached to a distal end of the housing and the needle holder is arranged to fit over a distal part of a medicament cartridge.

17. The medicament injection device of claim 16, wherein the medicament cartridge holder contains the medicament cartridge and axial movement of the medicament cartridge holder in the distal direction causes the proximal end of the needle to penetrate a penetrable barrier at the distal part of the medicament cartridge.

18. The method of claim 17, wherein axial movement of the medicament cartridge holder in the distal direction causes the needle holder to dock with the medicament cartridge.

19. The method of claim 16, further comprising moving the rotatable cap assembly in the distal direction to release the needle holder from the rotatable cap assembly.

* * * * *

UNITED STATES PATENT AND TRADEMARK OFFICE
CERTIFICATE OF CORRECTION

PATENT NO. : 11,351,309 B2
APPLICATION NO. : 16/344430
DATED : June 7, 2022
INVENTOR(S) : Markus Halm It is certified that error appears in the above-identified patent and that said Letters Patent is hereby corrected as shown below:

In the Claims

In Column 12, Line 23, Claim 17, delete "medicament injection device" and insert -- method --

Signed and Sealed this
Tenth Day of January, 2023

Katherine Kelly Vidal
*Director of the United States Patent and Trademark Office*